United States Patent [19]

Sugawara et al.

[11] Patent Number: 4,904,470
[45] Date of Patent: Feb. 27, 1990

[54] ANTIBIOTIC F-0769, PROCESS FOR ITS PRODUCTION, AND ITS USE AS A GROWTH ACCELERATING AND FEED EFFICIENCY INCREASING AGENT AND AS AN ANTITUMOUR AGENT

[75] Inventors: Hideo Sugawara, Toride; Tomonori Takashina, Chouhu; Nobuko Takahashi, Toda; Machiko Sugiyama, Kawaguchi; Akio Seino, Tokyo; Yukio Miyazaki, Ageo, all of Japan

[73] Assignee: Kaken Pharmaceutical Company, Ltd., Tokyo, Japan

[21] Appl. No.: 21,125

[22] Filed: Mar. 3, 1987

[30] Foreign Application Priority Data

Mar. 4, 1986 [JP] Japan .................... 61-45226

[51] Int. Cl.$^4$ .......................... A61K 35/74; C12P 1/06
[52] U.S. Cl. ...................................... 424/119; 435/169
[58] Field of Search .................... 424/119; 435/69, 169

[56] References Cited

PUBLICATIONS

"Antibiotic NRC-501, a New Antibiotic Produced by a Streptomyces Spec." Published on May 16, 1976.
"An Antibiotic Complex Derived from a Streptomyces and Active Against Gram-Positive Bactera" Published on Sep. 17, 1960.

Primary Examiner—Jerome D. Goldberg
Attorney, Agent, or Firm—Oblon, Spivak, McClelland, Maier, Neustadt

[57]  ABSTRACT

An antibiotic F-0769 having the following properties:
(1) Outer appearance: White or light yellow powder,
(2) Melting point: 245°–250° C.,
(3) Specific rotation: $[\alpha]_D^{25} = -37.5°$ (c=1, methanol),
(4) Solubility in solvents: Soluble in methanol, ethanol, acetone, chloroform, ethyl acetate and benzene; and insoluble in water and hexane,
(5) Elementary analysis (found %): C:57.53, H:7.36, O:21.17, N:12.97,
(6) Ultraviolet absorption spectrum (as measured in methanol: As shown in FIG. 1, $\lambda max(E_{1\ cm}^{1\%})=213$ nm (466), 286 nm (200)
(7) Infrared absorption spectrum (as measured by KBr method): As shown in FIG. 2,
(8) Nuclear magnetic resonance spectra (as measured in heavy chloroform): $^1$H-NMR spectrum is as shown in FIG. 3, and $^{13}$C-NMR spectrum is as shown in FIG. 4,
(9) Distinction among basicity, acidity and neutrality: Neutral substance,
(10) Amino acid analysis: As a result of the hydrolysis with 6N hydrochloric acid at 110° C. for 18 hours, amino acids i.e. threonine, valine and leucine were detected,
(11) Color reactions: Positive in the iodine reaction and in the potassium permanganate reaction; and negative in the ninhydrin reaction and in the ferric chloride reaction,
(12) Thin layer chromatography (by means of silica gel, Art, 5715, manufactured by Merck Co.):

| Solvent system | Rf value |
|---|---|
| Ethyl acetate | 0.16 |
| Ethyl acetate-methanol (5:1) | 0.33 |
| Chloroform-methanol (10:1) | 0.68 |
| Ethyl acetate-acetone (1:1) | 0.31 |
| Acetone-benzene (5:1) | 0.40 |

(13) Molecular weight (as measured by Rast method): About 745

7 Claims, 4 Drawing Sheets

ANTIBIOTIC F-0769, PROCESS FOR ITS PRODUCTION, AND ITS USE AS A GROWTH ACCELERATING AND FEED EFFICIENCY INCREASING AGENT AND AS AN ANTITUMOUR AGENT

The present invention relates to a novel antibiotic F-0769, a process for its production, and its use as a growth accelerating and feed efficiency increasing agent for domestic animals or fowls and as an antitumour agent.

The present inventors have isolated a number of microorganisms from various soils for the purpose of searching useful antibiotics and studied the antibiotics produced by the isolated microorganisms. As a result, they have found that when Streptomyces violaceusnigar F-0769 strain belonging to the genus Streptomyces isolated from paddy field soil collected in Kitaamarumemachi, Sakata-shi, Akita-ken, Japan, is cultured in a proper culture medium, an antibiotic having a high antibacterial activity against gram positive bacteria is accumulated in the culture medium. This antibiotic has been isolated and compared with known antibiotics in the physicochemical properties and biological properties, whereby it has been confirmed to be a new antibiotic and named antibiotic F-0769.

The present invention is based on this discovery, and provides the new antibiotic F-0769 and a process for its production which comprises culturing an antibiotic F-0769-producing microorganism belonging to the genus Streptomyces and isolating the antibiotic F-0769 from the culture product.

Further, the present invention provides a growth accelerating and feed efficiency increasing agent for domestic animals and fowls, which comprises the antibiotic F-0769 as the effective ingredient, and a method for accelerating the growth of domestic animals and fowls and increasing the feed efficiency thereof, which comprises administering an effective amount of the antibiotic F-0769 to the animals and fowls.

Furthermore, the present invention provides an antitumour agent comprising the antibiotic F-0769 as an active ingredient.

Now, the present invention will be described in detail with reference to the preferred embodiments.

In the accompanying drawings, FIG. 1 is the ultraviolet absorption spectrum of the antibiotic F-0769 as measured in methanol.

Figure 1:
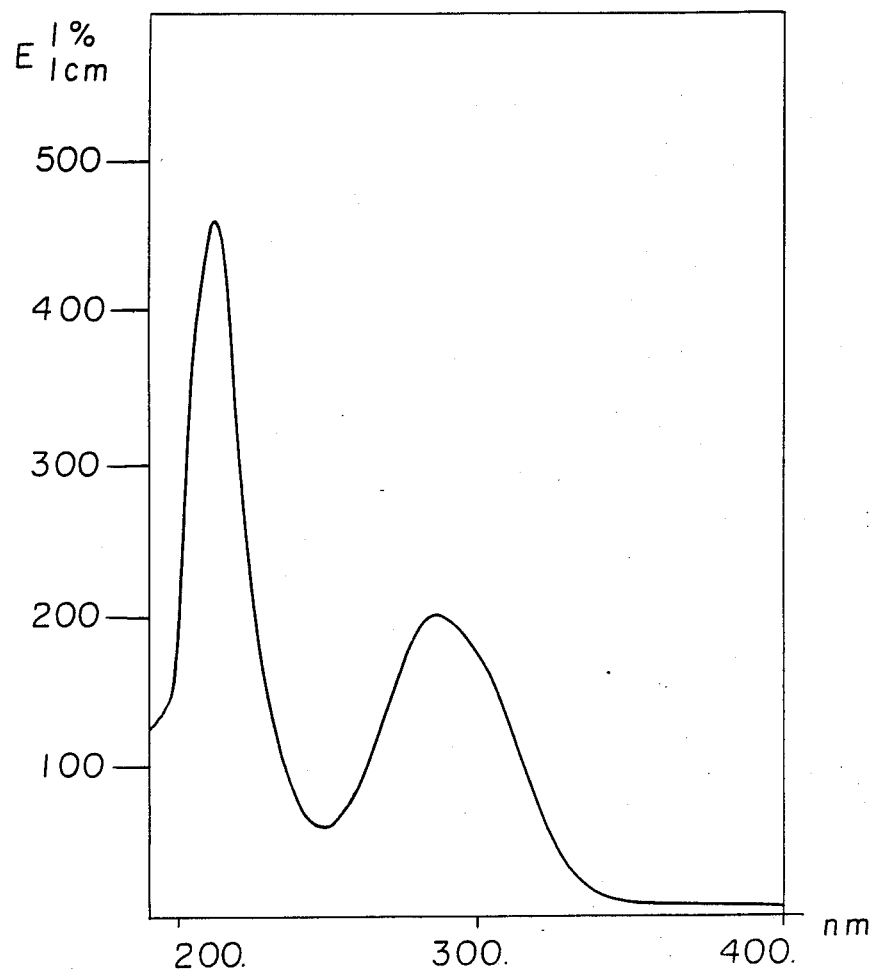

The microorganism which may be employed for the production of the antibiotic F-0769, may be any microorganism belonging to genus Streptomyces so long as it is capable of producing the antibiotic F-0769.

As a specific example of the microorganism used in the present invention, Streptomyces violaceusnigar F-0769 strain may be mentioned, which was deposited in Fermentation Research Institute of Japan on February 24, 1986 under Deposition No. FERM 8663, which was transferred to an international deposition on January 28, 1987 under FERM BP-1264.

Natural or artificial mutants of Streptomyces violaceusnigar F-0769 strain, other microorganisms belonging to genus Streptomyces or to any other genus, or microorganisms modified by gene manipulation to have a antibiotic F-0769 producing ability, may also be employed in the present invention so long as they are capable of producing the antibiotic F-0769.

The mycological characteristics of the F-0769 strain producing the antibiotic of the present invention, are as follows.

The F-0769 strain used in the present invention has branched mycelia, and aerial mycelia extending in air are fragmented to constitute ten or more spores which are spiral and have a rugose surface.

From the hydrolyzate of the whole cells, L,L-diaminopimeric acid is detected, but meso-diaminopimeric acid is not detected. As a sugar component, galactose is detected. However, arabinose, xylose and madurose are not detected. From these characteristics, the F-0769 strain is determined to be a strain belonging to genus Streptomyces among Actinomycetales Streptomycetaceae.

The Streptomyces violaceusnigar F-0769 strain has the following microbiological properties.

I. Morphological characteristics

The substratal mycelia are well developed and branched, whereby the diameter of each mycelium is about $1.5 \times 1.0$ μm. The surface of the culture swells and often forms wrinkles. The mycelia adhere well to several culture media such as a yeast-starch agar culture medium, a yeast-malt agar culture medium or a sucrose-nitrate agar culture medium. The aerial mycelia are well developed. The forward ends of the fragmented spores are spiral with coiling of an average of 4 or 5 times, and they constitute spore chains, but the boundaries between adjacent spores in the spore chains are not distinct. No sporangium, sclerotium or coremium is observed.

II. Cultural characteristics

The tests were conducted in accordance with the test method reported by E. B. Shirling et al. (International Journal of Systematic Bacteriology, 16, 313–340 (1966)). Additionally, known culture media and test methods were employed.

The color was determined under the standard light source of xenon lump by using Color Harmony Manual, 4th edition, 1958 as the color standards. When the corresponding color tab was found, it was shown by the common names first, and then the color tab code was shown in parenthesis.

Unless otherwise specified, the following data represent the growth condition as cultured for three weeks at 28° C. on a agar plate culture medium.

(1) Sucrose-nitrate culture medium (Difco-Czapeck's Solution Agar)

The growth is good. Light ivory-eggshell to mustard gold-old gold, bamboo chamois (2ca-2ne, 2gc). The aerial mycelia adhere slightly. No soluble pigment is observed.

(2) Glucose-asparagine culture medium

The strain grows well and spreads. Light wheat-light maize to bamboo chamois (2ea-2gc). The aerial mycelia adhere slightly and are off white. No soluble pigment is observed.

(3) Glycerol-asparagine culture medium (ISP-5, Difco)

The growth is no good and light ivory-eggshell. No aerial mycelia adhere. No soluble pigment is observed.

(4) Starch agar culture medium (ISP-4, Difco, Inorganic salt-starch agar)

The growth is initially good, but gradually deteriorates. Light ivory-eggshell. The aerial mycelia adhere well and are dusk (near gray 10fe). No soluble pigment is observed.

(5) Tyrosine agar culture medium (ISP-7, Difco, Tyrosine agar)

The strain grows well and spreads. Covert tan gray (2ge) to black. The aerial mycelia grow very well and are powdery. Melon yellow (3ga). No soluble pigment is observed.

(6) Nutrient agar medium

The growth is no good. The aerial mycelia do not substantially grow. No soluble pigment is observed.

(7) Yeast-malt extract agar culture medium (ISP-2, Difco, yeast-malt extract agar)

The strain grows very well and spreads. Mustard-old gold (21e) to topaz-butter scotch (3ne). No soluble pigment is observed.

(8) Oatmeal culture medium (ISP-3, Difco)

The strain grows well and spreads. Beige gray-mouse (near gray 3ih). The soluble pigment is light yellow.

(9) Yeast-starch agar culture medium

The growth is good, and the culture swells and spreads. Honey gold-light gold (2ic). The aerial mycelia grow very well. Black plum. No soluble pigment is observed.

III, Physiological characteristics (1) Growth temperature range (Yeast-starch agar culture medium, pH 7.2 prior to sterilization, by means of a temperature gradient incubator, growth in the second week): Optimum temperature: 30° C.–33.2° C., Growable temperature: 12–38.5° C.

(2) Liquefaction of gelatin (glucose-peptone-gelatin stab culture): Positive (3) Coagulation and peptonization of skim milk (Difco, Skim milk 28° C. and 37° C.):
28° C. Peptonization: Positive; Coagulation: Negative
37° C. Peptonization: Positive; Coagulation: Negative (4) Formation of melanine:
Tyrosine agar culture medium: Negative
Melanine-forming culture medium: Negative (One week later: Weakly positive)
Peptone-yeast-iron agar culture medium: Negative
Triptone-yeast extract broth culture medium: Negative (5) Solubility of adenin, xanthin, hypoxanthin, tyrosine:
Hypoxanthin, Tyrosin: Positive
Adenin: Weakly positive
Xanthin: Negative (6) NaCl tolerance (Yeast-starch agar culture medium + sodium chloride): Growth up to 4% (No growth at 7%)

(7) Carbon source utilization (Difco, Carbon utilization agar culture medium, 28° C. in the 2nd week)
Positive: D-glucose, D-xylose, D-fructose, sucrose, i-inositol, L-rhamunose, raffinose, D-mannitol, L-arabinose, salicin
Negative: None This strain has been identified to be a strain belonging to *Streptomyces violaceusnigar* since it well agrees to *Streotomyces violaceusnigar* (Waksman and Curtis) Waksman and Henrici in that the spore chains are spiral and the spore surface is rugose; in some culture media, a part of the aerial mycelia turns into wet black spots as the culturing time passes; the NaCl tolerance is 4% to less than 7%; and it utilizes all carbon sources. Thus, this strain has been named *Streptomyces violaceusnigar* F-0769.

The antibiotic F-0769 of the present invention can be produced by culturing *Streptomyces violaceusnigar* F-0769 strain in a culture medium containing nutrients which are commonly utilized by actinomyces. For instance, as the carbon sources, there may be used glucose, glycerol, sucrose, dextrin, starch, etc. As the nitrogen sources, there may be employed soybean meal, wheat embryo, peptone, meat extract, yeast extract, corn steep liquor, an ammonium salt, etc. Further, if necessary, inorganic salts such as calcium carbonate, potassium chloride, magnesium sulfate and phosphates may be used.

As a culturing method, a liquid culturing is suitable. The culturing conditions such as the cultivation temperature, time, etc. are selected so that they are suitable for the growth of the microorganism used, and for the production of the antibiotic at the maximum yield. The production of the antibiotic reaches the maximum when the cultivation with aeration-agitation is conducted at a cultivation temperature of from 25 to 35° C. for 92 to 144 hours.

The antibiotic F-0769 produced and accumulated in the culture medium may be isolated from the culture medium and purified by means of conventional methods. For example, a method of utilizing the difference in the solubility between the antibiotic and impurities, and a method of utilizing the difference in the adsorption may be used individually or in combination, or repeatedly.

The quantitative analysis of the antibiotic F-0769 produced and the determination of the active fraction were conducted by an agar plate method by using *Bacillus subtilis* ATCC 6633 strain as the test microorganism.

A typical example of the isolation and purification of the antibiotic F-0769 is as follows.

The antibiotic F-0769 exists in the culture medium and microbial cells. It can be extracted from the culture medium with ethyl acetate, butyl acetate, chloroform or the like by utilizing its solubility in an organic solvent. From the microbial cells, it may be extracted with water-containing acetone, and then the organic solvent is distilled off under reduced pressure. It can then be extracted from the residual aqueous solution with ethyl acetate. Both extracts are put together and then concentrated under reduced pressure to obtain a crude extract of the antibiotic F-0769.

Then, the crude product is purified by adsorption chromatography such as alumina or silica column chromatography. The active fraction is collected, concentrated and dried to obtain an antibiotic F-0769 having a higher purity.

Then, the product is further purified by a gel permeation column chromatography using Sephadex LH-20 (manufactured by Pharmacia), and the active fraction is concentrated and dried to obtain the antibiotic F-0769 having a still-higher purity in the form of powder.

The antibiotic F-0769 of the present invention thus obtained has the following physicochemical and biological properties.

(1) Outer appearance: White or light yellow powder,
(2) Melting point: 245–250° C.,
(3) Specific rotation: $[\alpha]25 = -37.5°$ (c=1, methanol), (4) Solubility in solvents: Soluble in methanol, ethanol, acetone, chloroform, ethyl acetate and benzene; and insoluble in water and hexane, (5) Elementary analysis (found %): C:57.53, H:7.36, O:21.17, N:12.97, (6) Ultraviolet absorption spectrum (as measured in methanol: As shown in FIG. 1, $\lambda$max-(E1%1cm)=213nm(466)286nm(200)

Figure 2:
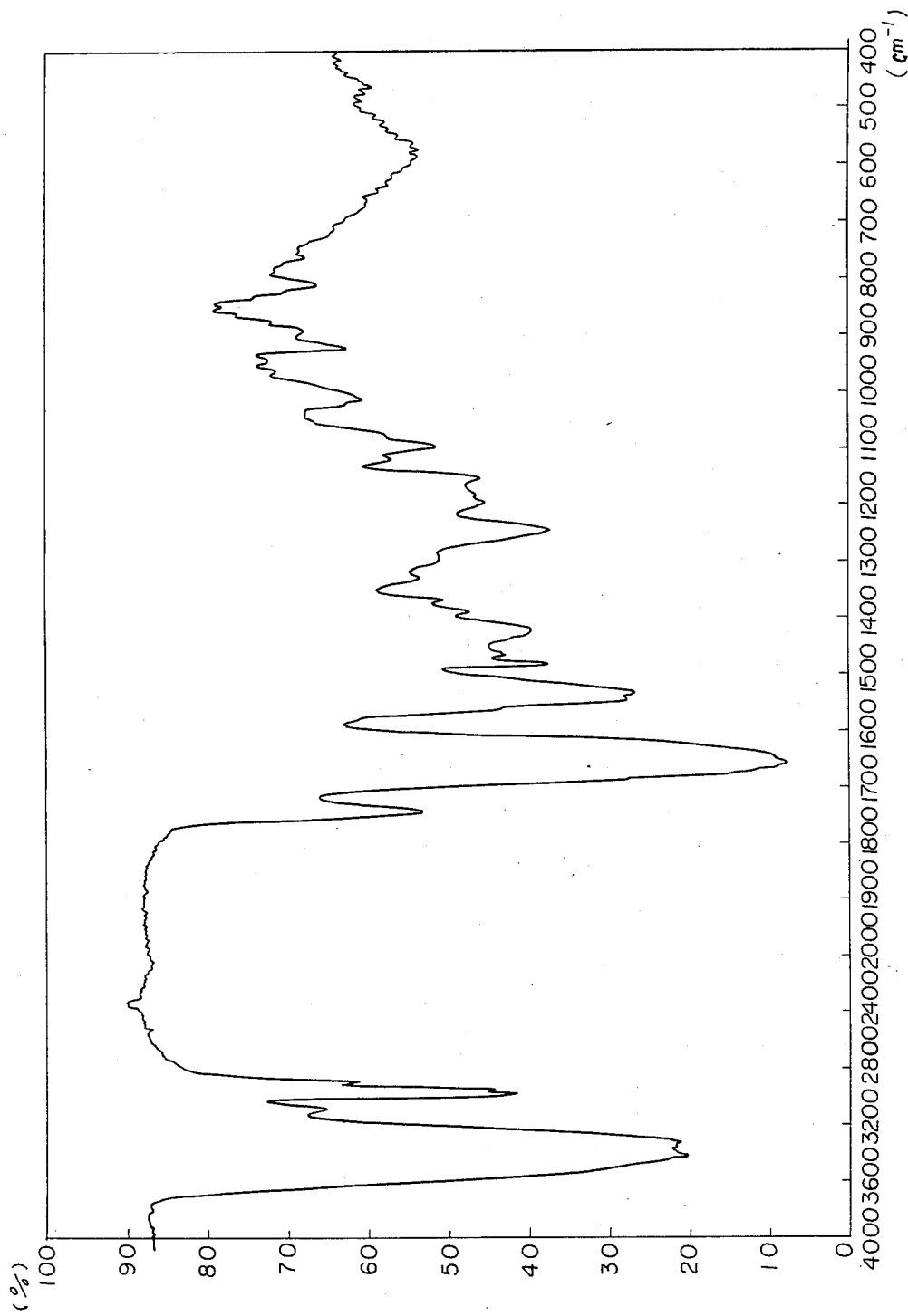
FIG. 2 is the infrared absorption spectrum of the antibiotic F-0769 as measured by a KBr method.
Figure 3:
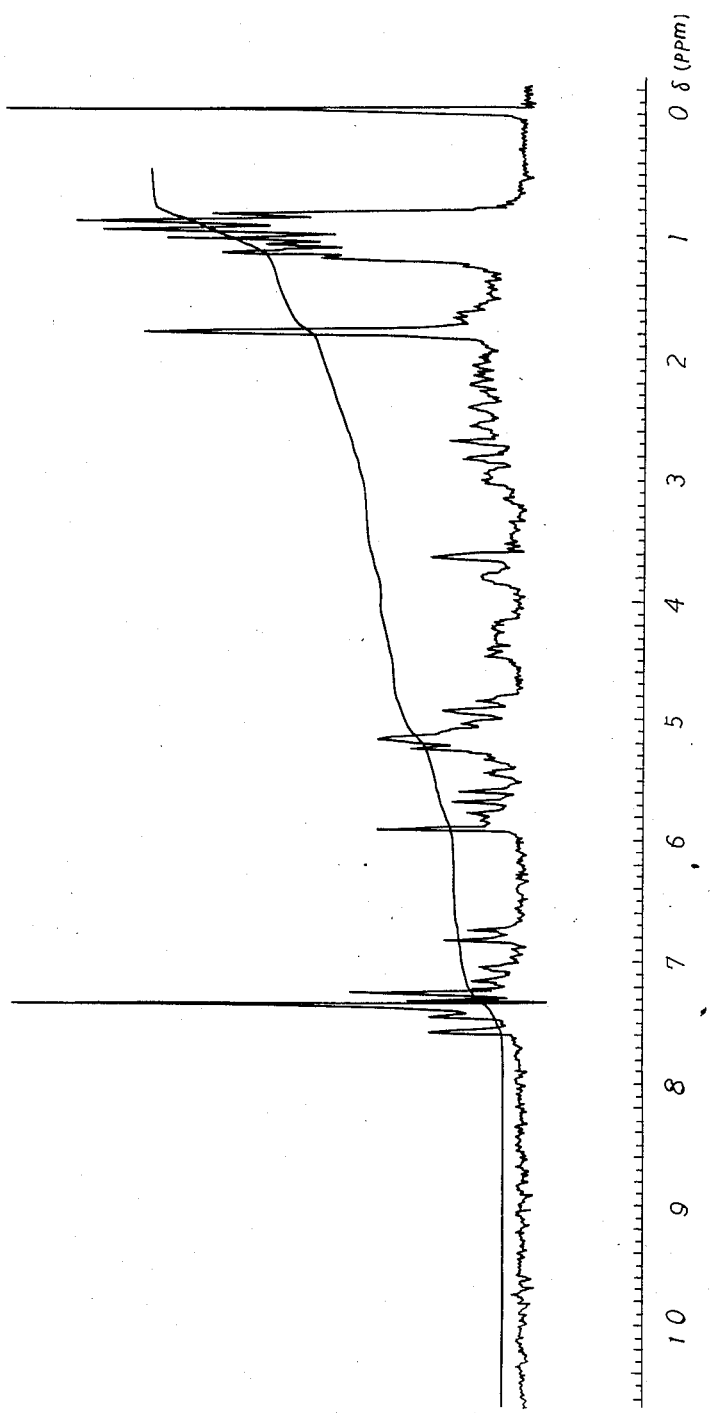
FIG. 3 is the $^1$H-NMR spectrum of the antibiotic F-0769 as measured in heavy chloroform.
Figure 4:
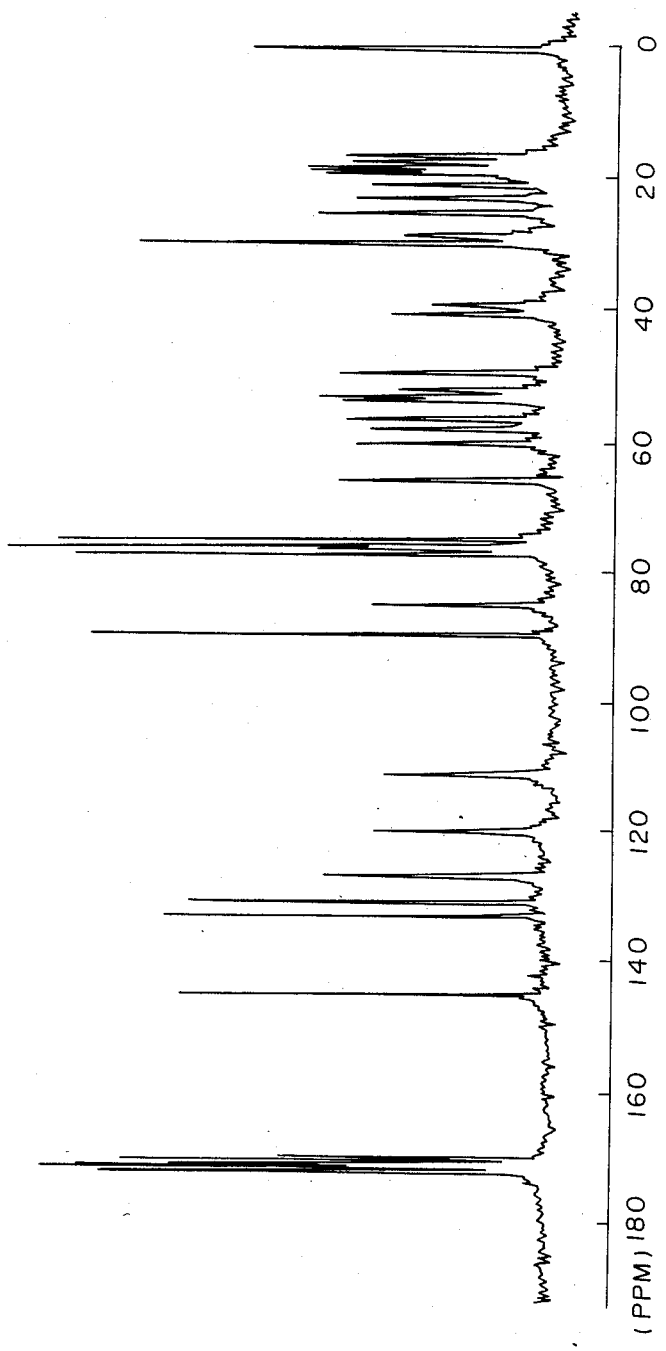
FIG. 4 is the $^{13}$C-NMR spectrum of the antibiotic F-0769 as measured in heavy chloroform.

(7) Infrared absorption spectrum (as measured by KBr method): As shown in FIG. 2, (8) Nuclear magnetic resonance spectra (as measured in heavy chloroform): $^1$H-NMR spectrum is as shown in FIG. 3, and $^{13}$C-NMR spectrum is as shown in FIG. 4, (9) Distinction among basicity, acidity and neutrality: Neutral substance,

(10) Amino acid analysis: As a result of the hydrolysis with 6N hydrochloric acid at 110° C. for 18 hours, amino acids i.e. threonine, valine and leucine were detected,

(11) Color reactions: Positive in the iodine reaction and in the potassium permanganate reaction; and negative in the ninhydrin reaction and in the ferric chloride reaction,

(12) Thin layer chromatography (by means of silica gel, Art. 5715, manufactured by Merck Co.):

| Solvent system | Rf value |
|---|---|
| Ethyl acetate | 0.16 |
| Ethyl acetate-methanol (5:1) | 0.33 |
| Chloroform-methanol (10:1) | 0.68 |
| Ethyl acetate-acetone (1:1) | 0.31 |
| Acetone-benzene (5:1) | 0.40 |

(13) Molecular weight (as measured by Rast method): About 745

(14) Antibacterial activities:

The antibacterial activities are shown in Table 1. The antibacterial activities were measured by an agar dilution method.

TABLE 1

| Test microorganism | Minimum inhibitory concentration ($\mu$g/ml) |
|---|---|
| Staphylococcus aureus FDA 209P JC-2 | 0.78 |
| Staphylococcus aureus Terajima | 0.78 |
| Staphylococcus aureus MS 353 | 0.78 |
| Streptococcus pyogenes Cook | 0.78 |
| Micrococcus luteus ATCC 9413 | 0.78 |
| Bacillus subtilis ATCC 6633 | 0.2 |
| Escherichia coli NIHJ JC-2 | >100 |
| Salmonella typhi | >100 |
| Serratia marcescens IAM 1184 | >100 |
| Proteus mirabilis IFO 3849 | >100 |
| Enterobacter cloacae 963 | >100 |
| Pseudomonas aeruginosa IFO 3445 | >100 |
| Candida albicans | >100 |
| Piricularia oryzae | >100 |
| Alternaria mali | >100 |
| Cochliobolus miyabeanus | >100 |
| Clostriridium perfringens B103-252 | 1.56 |
| Clostriridium difficile V-6 | 1.56 |
| Peptococcus prevotii V-72 | 1.56 |
| Eubacterium moniliforme V-45 | 1.56 |
| Eubacterium lentum 0612 | 1.56 |
| Bacteroides fragilis GM-7000 | >100 |
| Veillonella parvula 0574 | >100 |
| Fusobacterium varium B-1083 | >100 |

The antibiotic F-0769 exhibits high antibacterial activities against gram-positive bacteria.

The antibiotic F-0769 of the present invention is considered to belong to a general class of peptide antibiotics. However, from the comparison with known substances in the physicochemical and biological properties such as the ultraviolet absorption spectrum, the infrared absorption spectrum and the amino acid analysis, there has been no known substance which corresponds to the substance of the present invention. More specifically, there has been no other peptide antibiotic showing ultraviolet absorption at, 213 nm and 286 nm, which is a characteristic of the substance of the present invention. Antibiotic 1415 [Nature, 187(4742), 1029-1030(1960)]or antibiotic NRC-501 [Mikrobiol, 16, 337-343 (1976)]may be mentioned as a substance showing a similar absorption, but each of these antibiotics is different from the antibiotic substance of the present invention in the amino acid composition. Thus, the substance of the present invention has been determined to be a novel antibiotic.

The antibiotic F-0769 has particularly strong antibacterial effects against gram-positive bacteria, and is expected to be useful as an antibacterial agent or as a feed additive, especially as a growth accelerating and feed efficiency increasing agent for domestic animals and fowls, which comprises the antibiotic F-0769 as the effective ingredient, and a method for accelerating the growth of domestic animals and fowls and increasing the feed efficiency thereof, which comprises administering an effective amount of the antibiotic F-0769 to the animals and fowls.

Further, it has antitumour activities and is expected to be useful as an antitumour agent.

Now, the present invention will be described in further detail with reference to Examples. However, it should be understood that the present invention is by no means restricted to these specific Examples.

EXAMPLE (Production)

As a seed culture medium, a culture broth (pH7.8 prior to sterilization) comprising 1% of glucose, 3% of starch, 0.1% of meat extract, 0.4% of beer yeast, 0.2% of sodium chloride, 2.5% of soybean meal and 0.1% of calcium carbonate was used.

The seed culture medium was introduced in an amount of 70 ml into each of 500 ml Erlenmeyer flasks, and Streptomyces violaceusnigar F-0769 strain (FERM BP-1264) was inoculated to each Erlenmeyer flask and cultured under shaking at 28° C. for 48 hours.

Then, 1 liter of this seed culture broth was transplanted to a tank containing 100 liters of a culture medium for production.

The culture medium for production had a composition comprising 1.5% of glucose, 4.5% of starch, 0.1% of meat extract, 0.4% of beer yeast, 0.2% of sodium chloride, 2.5% of soybean meal, 0.1% of calcium carbonate, 0.05% of $CoCl_2.6H_2O$, 0.5% of $FeSO_4.7H_2O$ and 0.2% of a defoaming agent CA-123 (manufactured by Nippon Oil and Fat Co., Ltd.) (pH7.0 prior to sterilization). The culturing was conducted at 30° C. for 96 hours under stirring and aeration. The rate of aeration was 100 liters per minute, and the rotation of the stirrer was 200 r.p.m.

After the completion of the culturing, the culture broth was adjusted to pH 8.0, and after an addition of 4% of Celite as a filter aid, filtered to separate the filtrate and bacterial cells. To the cells, 100 liters of 90% acetone water was added and stirred for one hour. The mixture was filtered, and acetone was distilled off under reduced pressure to obtain 10 liters of an aqueous solution. This aqueous solution was combined with the culture filtrate, and extracted twice with 50 liters of ethyl acetate. The ethyl acetate extract was concentrated, and the concentrate was adsorbed on an alumina column (5.5 cm in diameter ×10 cm) preliminarily treated with ethyl acetate, and then developed with methanol, whereby an active fraction was eluted. The active fraction was collected, and concentrated under reduced pressure, whereby methanol was distilled off, to obtain about 75 g of an oily substance.

The antibiotic F-0769 in an amount of 0, 10 or 20 ppm was uniformly mixed with a perfect combination feed for chicks (manufactured by Oriental Yeast Co.).

Chickens used:

Each group of 10 female chickens of Shever-Star-Bro for meat, was freely fed with the feed for 8 weeks, and the body weight and the feed ingestion were measured. The results are shown in Table 2.

It was found that the feed demand index was improved by from 3 to 4% and the weight increase was improved by from 5 to 6% by the addition of the antibiotic F-0769 to the feed.

TABLE 2

| Group | Amount of antibiotic F-0769 added to the feed (ppm) | Average weight at the initiation of the test (g) | Average weight increase during the period (g) | Average amount of feed ingested during the test period (g) | Feed* demand index | Improvement** of the feed demand index (%) |
|---|---|---|---|---|---|---|
| 1 | 10 | 93.5 | 2,449.8 | 5,290.1 | 2.159 | 3.1 |
| 2 | 20 | 94.0 | 2,460.1 | 5,299.0 | 2.154 | 3.3 |
| 3 | 0 | 93.5 | 2,325.0 | 5,179.5 | 2.228 | — |

*Feed demand index = $\dfrac{\text{Average amount of feed ingested during the test period}}{\text{Average weight increase during the test period}}$

**Improvement in the feed demand index (%) =

$$\left(1 - \dfrac{\text{Feed demand index when F-0769 was added}}{\text{Feed demand index when no antibiotic was added}}\right) \times 100$$

Further, this oily substance was dissolved in a small amount of chloroform, adsorbed on a packed silica gel column with chloroform, and then developed with a solvent mixture of chloroform-methanol (100:3). The active fraction was concentrated under reduced pressure and dried to obtain 12 g of the antibiotic F-0769 as crude powder.

Then, 12 g of this crude powder was dissolved in a small amount of ethyl acetate, adsorbed on a packed silica gel column with ethyl acetate, and then developed with ethyl acetate. The active fraction was concentrated under reduced pressure and dried to obtain 3.3 g of crude powder of the antibiotic F-0769.

Further, 3.3 g of the crude powder thus obtained, was dissolved in methanol, and subjected to gel permeation through a packed Sephadex LH-20 column with methanol.

The active fraction was concentrated and dried to obtain 2.7 g of the antibiotic F-0769 as a white or light yellow powder (melting point: 245–250° C.).

FORMULATION EXAMPLE (Feed aditive)

Antibiotic F-0769: 1%
Corn starch: 99%

The two materials were pulverized and uniformly mixed to obtain a premixture containing 1% of the antibiotic F-0769.

Test Example 1

Feed efficiency test on chickens)

Tested agent and feed:

Test Example 2

Feed efficiency test on swine

Pigs used: Land race species

Basic feed:

(a) From the initiation of the test to four weeks later
60% of grain (corn, wheat, barley), 15% of soybean cake, 15% of animal-based feed (skimmilk powder, fish powder), and 10% of others (enzyme, calcium carbonate, potassium phosphate, sodium chloride, etc.)

(b) From 4 to 12 weeks
78% of grain (corn, miro, wheat), 13% of soybean cake, 5% fish powder and 4% of others (calcium carbonate, calcium phosphate, sodium chloride, etc.)

Method:

Thirty young pigs of 35 days old in an average were divided into three groups, each group consisting of ten pigs, so that the average weight would be substantially equal. The antibiotic F-0769 was added to the basic feed in an amount of 0, 5 and 10 ppm, respectively. And then the three groups of pigs were fed with the feeds, respectively, for 12 weeks. Then, the body weight and the feed ingestion were measured. The results are shown in Table 3.

It was found that the feed demand index was improved by from 4 to 6% and the weight increase was improved by from 5 to 8%, by the addition of the antibiotic F-0769 to the feeds.

TABLE 3

| Group | Amount of antibiotic F-0769 added to the feed (ppm) | Average weight at the initiation of the test (kg) | Average weight increase during the period (kg) | Average amount of feed ingested during the test period (kg) | Feed* demand index | Improvement** of the feed demand index (%) |
|---|---|---|---|---|---|---|
| 1 | 5 | 8.20 | 45.80 | 107.0 | 2.336 | 4.5 |
| 2 | 10 | 8.22 | 47.02 | 108.9 | 2.316 | 5.3 |

TABLE 3-continued

| Group | Amount of antibiotic F-0769 added to the feed (ppm) | Average weight at the initiation of the test (kg) | Average weight increase during the period (kg) | Average amount of feed ingested during the test period (kg) | Feed* demand index | Improvement** of the feed demand index (%) |
|---|---|---|---|---|---|---|
| 3 | 0 | 8.22 | 43.73 | 107.0 | 2.446 | — |

*Feed demand index = $\frac{\text{Average amount of feed ingested during the test period}}{\text{Average weight increase during the test period}}$

**Improvement in the feed demand index (%) =

$\left(1 - \frac{\text{Feed demand index when F-0769 was added}}{\text{Feed demand index when no antibiotic was added}}\right) \times 100$

Test Example 3

Feed efficiency of ruminant

Steers used: Holstein

Concentrated feed:

71.5% of grain (corn, miro, barley), 11.5% of chaff and bran (corn gluten feed, wheat bran, rice bran oil cake), 5.5% of vegetable oil cake (soybean cake, linseed oil cake), and 11.5% of others (alphalpha meal, molasses, calcium phosphate, sodium chloride)

Method:

Fifteen castrated Holstein steers of 8 months old were divided into three groups, each consisting of five steers, so that the average body weight will be substantially equal. The antibiotic F-0769 was added to the basic concentrated feed in an amount of 0, 7.5 and 15 ppm, respectively. The three groups of steers were fed with the feeds, respectively. Further, dried rice straw was fed as crude feed in an amount of 1 kg per steer. The results are shown in Table 4.

It was found that the feed demand index was improved by from 4 to 6% and the weight increase was improved by from 7 to 8%, b the addition of the antibiotic F-0769 to the feeds.

monensin or lasalocid, known as an anticoccidiosis agent for domestic fowls.

Further, it may be used also in combination with other antibacterial agents or hormone agents, or with other natural substances having feed efficiency increasing effects, their extracts, antibiotics or synthetic compounds.

Test Example 4

Antitumour activities

The antibiotic F-0769 was intraperitoneally administered to cancerous mice ($BDF_1$ mice) having p 388 tumour cells, and the antitumour activities were examined, whereby the antibiotic was found to show effective antitumour activities at a dose of from 0.08 mg/kg to 1.25 mg/kg.

The evaluation was made on the basis that the case where the ratio of the survival days of the treated group to the survival days of the non-treated group (i.e. T/C%) was at least 130%, was determined to be "effective". The results are shown in Table 5.

TABLE 4

| Group | Amount of antibiotic F-0769 added to the feed (ppm) | Average weight at the initiation of the test (kg) | Average weight increase during the period (kg) | Average amount of feed ingested during the test period (kg) | Feed* demand index | Improvement** of the feed demand index (%) |
|---|---|---|---|---|---|---|
| 1 | 7.5 | 321 | 301 | 2340 | 7.774 | 5.9 |
| 2 | 15 | 320 | 303 | 2382 | 7.861 | 4.8 |
| 3 | 0 | 323 | 281 | 2320 | 8.256 | — |

*Feed demand index = $\frac{\text{Average amount of feed ingested during the test period}}{\text{Average weight increase during the test period}}$

**Improvement in the feed demand index (%) =

$\left(1 - \frac{\text{Feed demand index when F-0769 was added}}{\text{Feed demand index when no antibiotic was added}}\right) \times 100$ From the foregoing Test Examples, the antibiotic of the present invention is expected to be useful as a feed additive.

The concentration of the antibiotic F-0769 as the feed efficiency increasing agent, varies depending upon the kind or age of the animals or fowls or upon the season or timing for feeding. However, it is usually within a range of from 1 to 200 ppm, preferably from 2 to 100 ppm.

It may be mixed to the feed directly, or after being formulated into a proper form with a carrier or adjuvant. Otherwise, it may be administered as incorporated in drinking water.

Depending upon the kind of the animals or fowls, it may be used in combination with another agent, for example, with another antibiotic such as salinomycin,

TABLE 5

| Dose of F-0769 (mg/kg) | T/C (%) | Evaluation |
|---|---|---|
| 1.25 | 133 | Effective |
| 0.625 | 133 | Effective |
| 0.313 | 133 | Effective |
| 0.156 | 133 | Effective |
| 0.080 | 133 | Effective |

From the above results, the antibiotic F-0769 is expected to be useful as an antitumour agent. Test Example 5: Acute toxicity The acute toxicity was determined by survival or death upon expiration of 2 weeks after administration by using JCL/ICR male mice (5 weeks old, body weight: 21-23 g). The $LD_{50}$ (intraperetoneal administration) was about 20 mg/kg.

We claim:

1. An antibiotic F-0769 having the following properties:
   (1) Outer appearance: White or light yellow powder,
   (2) Melting point: 245-250° C.,
   (3) Specific rotation: [α]25=−37.5° (c=1, methanol),
   (4) Solubility in solvents: Soluble in methanol, ethanol, acetone, chloroform, ethyl acetate and benzene; and insoluble in water and hexane,
   (5) Elemental analysis (found %): C:57.53, H:7.36, O:21.17, N:12.97,
   (6) Ultraviolet absorption spectrum (as measured in methanol): As shown in FIG. 1, λmax-(e1%1cm)=213nm (466nm (200)
   (7) Infrared absorption spectrum (as measured by KBr method): As shown in FIG. 2,
   (8) Nuclear magnetic resonance spectra (as measured in heavy chloroform): $^1$H-NMR spectrum is as shown in FIG. 3, and $^{13}$C-NMR spectrum is as shown in FIG. 4,
   (9) Distinction among basicity, acidity and neutrality: Neutral substance,
   (10): Amino acid analysis: As a result of the hydrolysis with 6N hydrochloric acid at 110° C. for 18 hours, amino acids i.e. threonine, valine and leucine were detected,
   (11) Color reactions: Positive in the iodine reaction and in the ninhydrin reaction and in the ferric chloride reaction,
   (12) Thin layer chromatography (by means of silica gel, Art. 5715, manufactured by Merck Co.):

| Solvent system | Rf value |
|---|---|
| Ethyl acetate | 0.16 |
| Ethyl acetate-methanol (5:1) | 0.33 |
| Chloroform-methanol (10:1) | 0.68 |
| Ethyl acetate-acetone (1:1) | 0.31 |
| Acetone-benzene (5:1) | 0.40 |

(13) Molecular weight (as measured by Rast method): About 745.

2. A method for accelerating the growth of domestic animals and fowls and increasing the feed efficiency thereof which comprises administering an effective amount of the antibiotic F-0769 as defined in claim 1 to the animals and fowls.

3. A growth accelerating and feed efficiency increasing agent for domestic animals and fowls, comprising an effective amount of antibiotic F-0769 as defined in claim 1 as an effective ingredient in combination with a suitable carrier material.

4. A pharmaceutical composition comprising an effective amount of antibiotic F-0769 as defined in claim 1, as an active ingredient, together with a pharmaceutically acceptable carrier material.

5. A process for producing antibiotic F-0769, comprising:
   culturing an antibiotic F-0769-producing microorganism belonging to the genus Streptomyces violaceusnigar F-0769 in a culture medium containing, as a carbon source, glucose, glycerol, sucrose, dextrin or starch, and as a nitrogen source, soybean meal, wheat embryo, peptone, meat extract, yeast extract, corn steep liquor or an ammonium salt, until a sufficient amount of said antibiotic has been imparted to said medium and isolating antibiotic F-0769 from the culture product by a method which utilizes the difference in solubility between the antibiotic and impurities in the culture product or a method which utilizes the difference in absorption between the antibiotic and impurities in the culture product, or a combination of these, and
   obtaining antibiotic F-0769 characterized by the following properties:
   (1) physical appearance: white or light yellow powder;
   (2) melting point: 245° to 250° C.;
   (3) specific rotation: [α]25D=−37.5° (c=1, methanol);
   (4) solubility in solvents; soluble in methanol, ethanol, acetone, chloroform, methylacetate and benzene; and insoluble in water and hexane;
   (5) elemental analysis (percent found): C=57.53, H=7.36, O=21.17, N=12.97;
   (6) ultraviolet absorption spectrum (as measured in methanol: as shown in FIG. 1, $\lambda_{max}$(E1% 1cm)=213nm (466), 286nm (200));
   (7) infrared absorption spectrum (as measured by KBr method): as shown in FIG. 2;
   (8) nuclear magnetic resonance spectrum (as measured in CDCl$_3$): $^1$H-NMR spectrum as shown in FIG. 3, and $^{13}$C-NMR spectrum as shown in FIG. 4);
   (9) distinction among basicity, acidity and neutrality: neutral substance;
   (10) amino acid analysis: as a result of hydrolysis with 6N hydrochloric acid at 110° C. for 18 hours, detection of threonine, valine and leucine;
   (11) color reactions: positive in the iodine reaction and in the potassium permanganate reaction; and negative in the ninhydrin reaction and in the ferric chloride reaction;
   (12) thin layer of chromatography by means of silica gel, Art. 5715, manufactured by Merck Co.):

| Solvent system | Rf value |
|---|---|
| Ethyl acetate | 0.16 |
| Ethyl acetate-methanol (5:1) | 0.33 |
| Chloroform-methanol (10:1) | 0.68 |
| Ethyl acetate-acetone (1:1) | 0.31 |
| Acetone-benzene (5:1) | 0.40 |

(13) molecular weight (as measured by the Rast method): about 745.

6. The process of claim 5, comprising cultivating said microorganism at a cultivation temperature of from 25° to 35° C. for a length of time of 92 to 144 hours.

7. The process of claim 5, comprising using inorganic salts in said culture medium, said salts comprising calcium carbonate, potassium chloride, magnesium sulfate and phosphate.

* * * * *